US00PP11763P2

(12) United States Plant Patent
Cunneen

(10) Patent No.: US PP11,763 P2
(45) Date of Patent: Feb. 6, 2001

(54) ARGYRANTHEMUM PLANT NAMED 'SUMMER MELODY'

(75) Inventor: Thomas Michael Cunneen, Theresa Park (AU)

(73) Assignee: University of Sydney Plant Breeding Institute, Cobbitty, Cobbitty (AU)

( * ) Notice: Under 35 U.S.C. 154(b), the term of this patent shall be extended for 0 days.

(21) Appl. No.: 09/257,093

(22) Filed: Feb. 22, 1999

(51) Int. Cl.[7] ..... A01H 5/00
(52) U.S. Cl. ..... Plt./263
(58) Field of Search ..... Plt./263

(56) References Cited

PUBLICATIONS

UPOV–ROM GTITM Computer Database 2000/02, GTI JOUVE Retrieval Softward, citations for 'Summer Melody', 2000.*

Variety: 'Summer Melody'. Plant Varieties Journal vol. 13 (1): p. 25–27, 2000.*

* cited by examiner

*Primary Examiner*—Bruce R. Campell
*Assistant Examiner*—Wendy Baker
(74) *Attorney, Agent, or Firm*—C. A. Whealy

(57) ABSTRACT

A distinct cultivar of Marguerite Daisy plant named Summer Melody, characterized by its upright, mounding and compact plant habit; green-colored stems; small numerous leaves; freely branching, dense plants with short internodes; freely flowering with numerous inflorescences per plant; double-type inflorescences; and pinkish lavender ray florets and purple-tipped disc florets that give a dark "eye" effect to the inflorescence.

1 Drawing Sheet

BACKGROUND OF THE INVENTION

The present invention relates to a new and distinct cultivar of Marguerite Daisy plant, botanically known as *Argyranthemum frutescens* and referred to by the cultivar name Summer Melody.

The new cultivar is a product of a planned breeding program conducted by the Inventor in Cobbitty, New South Wales, Australia. The objective of the breeding program was to develop compact, early and freely-flowering Marguerite daisies that have inflorescences with good form and floret color.

The new cultivar originated from a cross made by the Inventor in 1995 of a proprietary selection of *Argyranthemum frutescens* identified as number X943817.2, as the male or pollen parent, with a proprietary selection of *Argyranthemum frutescens* identified as number X94147.1, as the female or seed parent. The cultivar Summer Melody was discovered and selected by the Inventor as a flowering plant within the progeny of the stated cross in a controlled environment in Cobbitty, New South Wales, Australia.

Plants of the new Marguerite Daisy are different from plants of the male parent, the selection number X943817.2, in plant height and inflorescence form.

Plants of the new Marguerite Daisy are different from plants of the female parent, the selection number X94147.1, in plant height, inflorescence form, ray floret color and time to flower.

Asexual reproduction of the new cultivar by terminal cuttings in Cobbitty, New South Wales, Australia, has shown that the unique features of this new Marguerite Daisy are stable and are reproduced true to type in successive propagations.

SUMMARY OF THE INVENTION

The new cultivar has not been observed under all possible environmental conditions. The phenotype may vary somewhat with variations in environment such as temperature, daylength and light intensity, without, however, any variance in genotype.

The following characteristics have been repeatedly observed and are determined to be basic characteristics of 'Summer Melody' which distinguish 'Summer Melody' as a new and distinct cultivar:

1. Upright, mounding and compact plant habit.
2. Green-colored stems; no anthocyanin.
3. Small numerous leaves.
4. Freely branching, dense plants with short internodes.
5. Freely flowering with numerous inflorescences per plant held above the foliage.
6. Double-type inflorescences.
7. Pinkish lavendar ray florets and purple-tipped disc florets that give a dark "eye" effect to the inflorescence.

Plants of the new Marguerite Daisy can be compared to plants of the anemone-type cultivar Double Pink, not patented. In side-by-side comparisons conducted in Cobbitty, New South Wales, Australia, plants of the new Marguerite Daisy are more compact, flower earlier and have smaller inflorescences than plants of the cultivar Sugar and Ice.

Plants of the new Marguerite Daisy can also be compared to plants of the cultivar Rosaline, not patented. In side-by-side comparisons conducted in Cobbitty, New South Wales, Australia, plants of the new Marguerite Daisy are more compact, flower earlier, have larger inflorescences and are more resistant to two-spotted mites than plants of the cultivar Rosaline.

BRIEF DESCRIPTION OF THE PHOTOGRAPHS

The accompanying colored photographs illustrate the overall appearance of the new cultivar, showing the colors as true as it is reasonably possible to obtain in colored reproductions of this type.

The photograph at the top of the sheet comprises a side perspective view of four typical plants of 'Summer Melody' in a 25-cm container.

The photograph at the bottom of the sheet comprises close-up views of developing inflorescences (top) and upper and lower leaf surfaces (bottom). Floret and foliage colors in the photographs may appear different from the actual colors due to light reflectance.

DETAILED BOTANICAL DESCRIPTION

The following observations, measurements and values describe a 25-cm container of four plants of the new Marguerite Daisy grown in Bonsall, Calif., in full sun with day temperatures ranging from 18 to 35° C. and night temperatures ranging from 13 to 18° C.

Color references are made to The Royal Horticultural Society Colour Chart except where general terms of ordinary dictionary signficance are used.

Botanical classification: *Argyranthemum frutescens* cultivar Summer Melody.

Parentage:

*Male or pollen parent.*—Proprietary selection of *Argyranthemum frutescens*, identified as number X943817.2.

*Female or seed parent.*—Proprietary selection of *Argyranthemum frutescens*, identified as number X94147.1.

Propagation:

*Type.*—Terminal cuttings.

*Time to initiate roots.*—Summer: About 10 days at a temperatures of 25° C. Winter: About 15 days at a temperatures of 20° C.

*Time to develop roots.*—Summer: About 15 days at a temperature of 25° C. Winter: About 20 days at a temperature of 20° C.

*Rooting habit.*—Numerous, fibrous to thick, and freely branching.

Plant description:

*General appearance.*—Inverted triangle; upright, mounding and compact plant habit. Short internodes and numerous leaves result in a compact, dense and full plant habit. Pinnatifid foliage and erect flower stems that hold the inflorescences above the foliage. Appropriate for various sizes and types of containers.

*Crop time.*—About 8 to 12 weeks are required to produce a finished flowering plant in a 10-cm container from a rooted cutting.

*Plant height.*—About 28 cm from soil level to top of inflorescences.

*Plant width.*—About 17 cm.

*Branching.*—Freely basal branching, about eight lateral per plant; removal of the terminal apex (pinching) is usually not required.

*Vigor.*—Low to moderately vigorous.

*Lateral branches.*—Length: About 23 cm. Diameter: About 5 mm. Internode length: About 5 mm. Texture: Glabrous; woody at base.

*Stem color.*—Green, 143C, no anthocyanin.

*Foliage description.*—Arrangement: Alternate, single. Quantity of leaves per lateral branch: Numerous, about 35 to 40 on primary laterals; about 25 leaves on secondary laterals. Shape: Pinnatifid. Apex: Three-parted. Base: Attenuate; clasping; sessile. Margin: Five to seven-lobed; deeply incised. Length: About 5.4 cm. Width: About 1.7 to 2 cm. Texture: Glabrous and smooth. Durability to stresses: Good, very durable. Leaves have a waxy cuticle that resists water loss. Color: Young leaves, upper surface: 138A. Young leaves, lower surface: 138B. Mature leaves, upper surface: 138A. Mature leaves, lower surface: More yellow than 137B. Venation, upper surface: 138C. Venation, lower surface: 138B.

Flowering description:

*Flowering habit.*—Inflorescences on long peduncles held above the foliage. Flat, double-type composite inflorescence form. Inflorescences form at upper leaf axils. Florets arranged acropetally on a capitulum. Inflorescences last about one week. Inflorescences persistent.

*Quantity of inflorescences.*—Freely flowering; typically about 5 to 7 inflorescences and buds per lateral stem; usually about 25 to 35 inflorescences and buds per plant.

*Natural flowering season.*—Natural flowering season is spring to early fall. Plants flower continuously during this period.

*Inflorescence size.*—Diameter: About 2.8 cm. Depth (height): About 1.2 cm. Disc diameter: About 3 mm.

*Fragrance.*—None.

*Ray florets.*—Aspect: Flat. Quantity per inflorescence and arrangement: About 105 ray florets arranged in multiple whorls. Shape: Ligulate. Apex: Very slightly tri-dentate. Base: Attenuate. Margin: Entire. Length, outer florets: About 1.6 cm. Width, outer florets: About 1.5 to 4 mm. Texture: Smooth, velvety. Color: When opening, upper surface: 69A. When opening, lower surface: 69B to 69C. Fully opened, upper surface: 75B to 77C to 74C; fading to 75D with subsequent development. Fully opened, lower surface: 75D.

*Disc florets.*—Shape: Tubular; 5-lobed. Quantity per inflorescence: Sparse, usually about 16. Disc floret length: About 5 to 10 mm. Disc floret width: About 1 mm. Color: Immature: 157A. Mature: 157C; apices, 71B, which gives a dark "eye" effect to the inflorescence.

*Phyllaries.*—Quantity per inflorescence and arrangement: About 15 per inflorescence; imbricate, three rows; tightly pressed to the receptacle. Aspect: Cupped. Shape: Elliptic. Apex: Broadly acute. Margin: Entire, outer edges slightly membranous. Length: About 5 mm. Color: Upper surface: 143C. Lower surface: 143A.

*Peduncle.*—Length, first peduncle: About 9 cm. Length, fourth peduncle: About 10 cm. Strength: Moderately strong, inflorescences held above foliage. Angle: Acute. Texture: Smooth. Color: 144C.

*Inflorescence bud.*—Shape: Ovoid. Length: About 1 cm. Diameter: About 6 mm. Color: 65D.

*Reproductive structures.*—Androecium: Stamens: About five, very tiny rudimentary stamens in central disc florets only; functionally sterile. Pollen: None observed. Gynoecium: Present on ray florets only. Pistil number: One per floret. Pistil length: About 3 mm. Style length: About 1.5 mm. Style color: 10A.

Stigma shape: Bilobed. Stigma color: 10A. Ovary color: 145B.

Disease resistance: Resistance to pathogens common to Argyranthemum has not been observed.

Seed production: Seed production is typically not observed.

It is claimed:

1. A new and distinct Marguerite Daisy plant named 'Summer Melody', as illustrated and described.

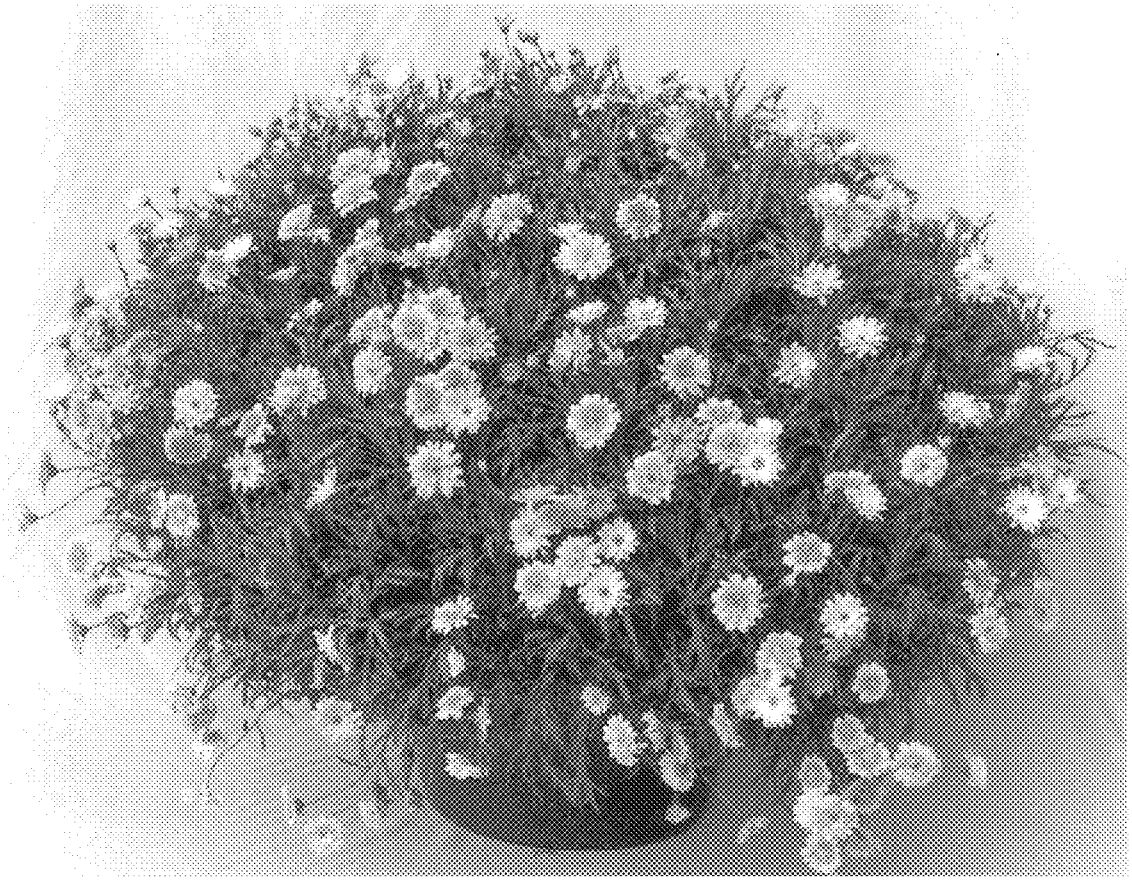
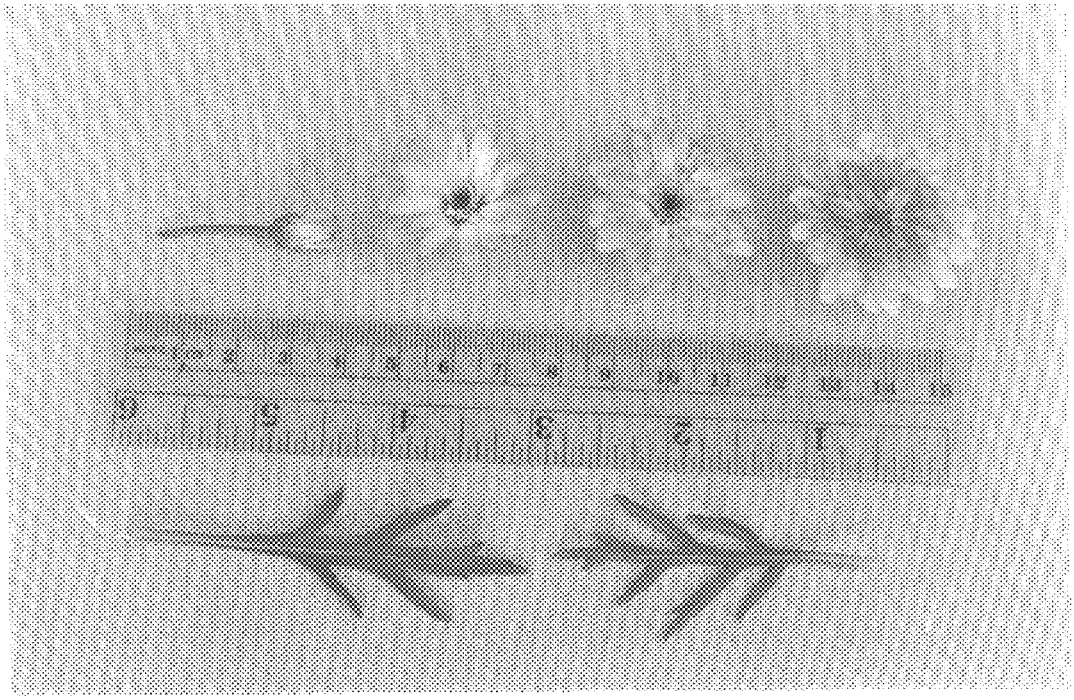

* * * * *